US00PP12687P2

(12) United States Plant Patent
Ullrich

(10) Patent No.: US PP12,687 P2
(45) Date of Patent: Jun. 11, 2002

(54) CHRYSANTHEMUM PLANT NAMED 'RED PIRANGA'

(75) Inventor: Peter F. Ullrich, Coral Gables, FL (US)

(73) Assignee: Flores Esmeralda Ltda., La Ceja-Antioquia (CO)

( * ) Notice: Subject to any disclaimer, the term of this patent is extended or adjusted under 35 U.S.C. 154(b) by 0 days.

(21) Appl. No.: 09/664,133

(22) Filed: Sep. 19, 2000

(51) Int. Cl.[7] ..... A01H 5/00
(52) U.S. Cl. ..... Plt./293

(58) Field of Search ..... Plt./293

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Red Piranga', characterized by its decorative-type inflorescences that are about 6.3 cm in diameter; dark purple to dark red-colored ray florets; uniform flowering habit; response time about 63 days; dark green foliage; strong stems; and good postproduction longevity with inflorescences maintaining good substance and color for almost three weeks in an interior environment.

2 Drawing Sheets

BACKGROUND OF THE INVENTION

The present invention relates to a new and distinct cultivar of Chrysanthemum plant, botanically known as *Dendranthema grandiflora* and referred to by the cultivar name Red Piranga.

The new Chrysanthemum was discovered by the Inventor in a controlled environment La Ceja-Antioquia, Colombia as a naturally-occurring whole plant mutation of the Chrysanthemum cultivar Piranga disclosed in U.S. Plant Pat. No. 6,889. The selection of this plant was based on its dark purple to dark red-colored ray florets compared to the red-colored ray florets of plants of the cultivar Piranga.

Asexual reproduction of the new Chrysanthemum by terminal cuttings taken in a controlled environment in La Ceja-Antioquia, Colombia, has shown that the unique features of this new Chrysanthemum are stable and reproduced true to type in successive generations.

SUMMARY OF THE INVENTION

The cultivar Red Piranga has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Red Piranga'. These characteristics in combination distinguish 'Red Piranga' as a new and distinct cultivar:

1. Decorative-type inflorescences that are about 6.3 cm in diameter.
2. Dark purple to dark red-colored ray florets.
3. Uniform flowering habit.
4. Response time about 63 days.
5. Dark green foliage.
6. Strong stems.
7. Good postproduction longevity with inflorescences maintaining good substance and color for almost three weeks in an interior environment.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the first sheet comprises a side perspective view of a typical flowering stem of 'Red Piranga' grown as a spray-type cut Chrysanthemum.

The photograph at the bottom of the first sheet comprises a close-up view of typical inflorescences of 'Red Piranga'.

The photograph at the top of the second sheet is a close-up view of a typical inflorescence of 'Red Piranga'.

The photograph in the middle of the second sheet comprises a close-up view of typical inflorescences of 'Red Piranga' (left) and 'Piranga' (right).

The photograh at the bottom of the second sheet comprises a close-up view of typical inflorescences of 'Red Piranga' (left) and 'Piranga' (right).

DETAILED BOTANICAL DESCRIPTION

The following observations and measurements describe plants grown in La Ceja-Antioquia, Colombia, under conditions which approximate commercial practice in a single-layer polyethylene-covered greenhouse. Rooted cuttings were planted in November, 1999, and received 13 long day/short nights followed by short day/long nights until flowering. Plants were grown as single-stem cut chrysanthemums. During the production time, the following environmental conditions were measured: day temperatures averaged 20° C.; night temperatures averaged 11.5° C.; and light level was about 3,500 foot-candles. Measurements and numerical values represent averages for six typical flowering stems. Color references are made to The Royal Horticultural Society Colour Chart except where general terms of ordinary dictionary significance are used.

Botanical classification: *Dendranthema grandiflora* cultivar Red Piranga.

Commercial classification: Decorative spray-type cut Chrysanthemum.

Parentage: Naturally-occurring whole plant mutation of *Dendranthema grandiflora* cultivar Piranga, disclosed in U.S. Plant Pat. No. 6,889.

Propagation:

*Type.*—Terminal tip cuttings.

*Time to produce a rooted cutting.*—Summer: About 9 to 10 days with temperatures at 23° C. Winter: About 10 to 11 days with temperatures at 13° C.

*Root description.*—Fine, fibrous and well-branched.

Plant description:

*Appearance.*—Herbaceous decorative spray-type cut flower. Stems upright, uniform habit and freely branching.

*Flowering stem length.*—About 90 cm.

*Stem color.*—Close to 146A.

*Foliage description.*—Arrangement: Alternate. Length: About 7.3 cm. Width: About 4.4 cm. Apex: Mucronate. Base: Attenuate to truncate. Margin: Palmately lobed; sinuses mostly divergent. Texture: Upper and lower surfaces slightly pubescent. Veins prominent on lower surface. Color: Young foliage, upper surface: Darker than 147A. Young foliage, lower surface: Darker than 147B. Mature foliage, upper surface: 147A. Mature foliage, lower surface: 147B. Venation, upper surface: 147B. Venation, lower surface: 147B. Petiole: Length: About 2.1 cm. Diameter: About 2.5 mm. Color, upper and lower surface: Close to 147B.

Inflorescence description:

*Appearance.*—Decorative spray-type inflorescence form with elongated oblong-shaped ray florets. Inflorescences borne on terminals, arising from leaf axils. Disc and ray florets arranged acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 63 days later; uniform flowering habit.

*Postproduction longevity.*—In an interior environment, flowering stems will maintain good color and substance for about two to three weeks in an interior environment.

*Quantity of inflorescences.*—About 7 inflorescences per flowering stem.

*Inflorescence size.*—Diameter: About 6.3 cm. Depth (height): About 2 cm. Diameter of dics: About 3 mm, inconspicuous. Diameter of receptacle: About 1 cm.

*Ray florets.*—Shape: Elongated oblong. Length: About 3.3 cm. Width: About 7 mm. Apex: Emarginate. Base: Attenuate; short corolla tube. Margin: Entire. Texture: Smooth, velvety, glabrous. Aspect: Initially upright, then perpendicular to peduncle; initially concave, then convex. Number of ray florets per inflorescence: About 224. Color: When opening, upper surface: Close to 4A to 4B becoming dark red purple, close to 185A. When opening, lower surface: Dark reddish purple, close to 187A to 187B. Fully opened, upper surface: Dark purple, close to 185A, becoming dark red, 46A, with subsequent development. Fully opened, lower surface: Base, close to 5A; mid-section, combination of alternating yellow, 5A, and dark purple to dark red, 187A to 185A to 46A, longitudinal stripes; apex, 187A to 185A to 46A.

*Disc florets.*—Shape: Tubular. Length: About 6 mm. Width: Apex: About 1.25 mm. Base: About 1 mm. Number of disc florets per inflorescence: Typically less than 10. Color: Immature: 154A. Mature: Apex: Close to 5A. Mid-section and base: 155D.

*Peduncle.*—Aspect: Strong, angled about 45° to the stem. Length: First peduncle: About 14.5 cm. Fourth peduncle: About 21 cm. Texture: Pubescent. Color: Close to 146A.

*Reproductive organs.*—Androecium: Present on disc florets only. Anther color: 12A. Pollen: Scarce. Pollen color: 12A. Gynoecium: Present on both ray and disc florets.

*Seed.*—Seed production has not been observed.

Disease resistance: Resistance to diseases common to Chrysanthemums has not been observed on plants grown under commercial conditions.

It is claimed:

1. A new and distinct cultivar of Chrysanthemum plant named 'Red Piranga', as illustrated and described.

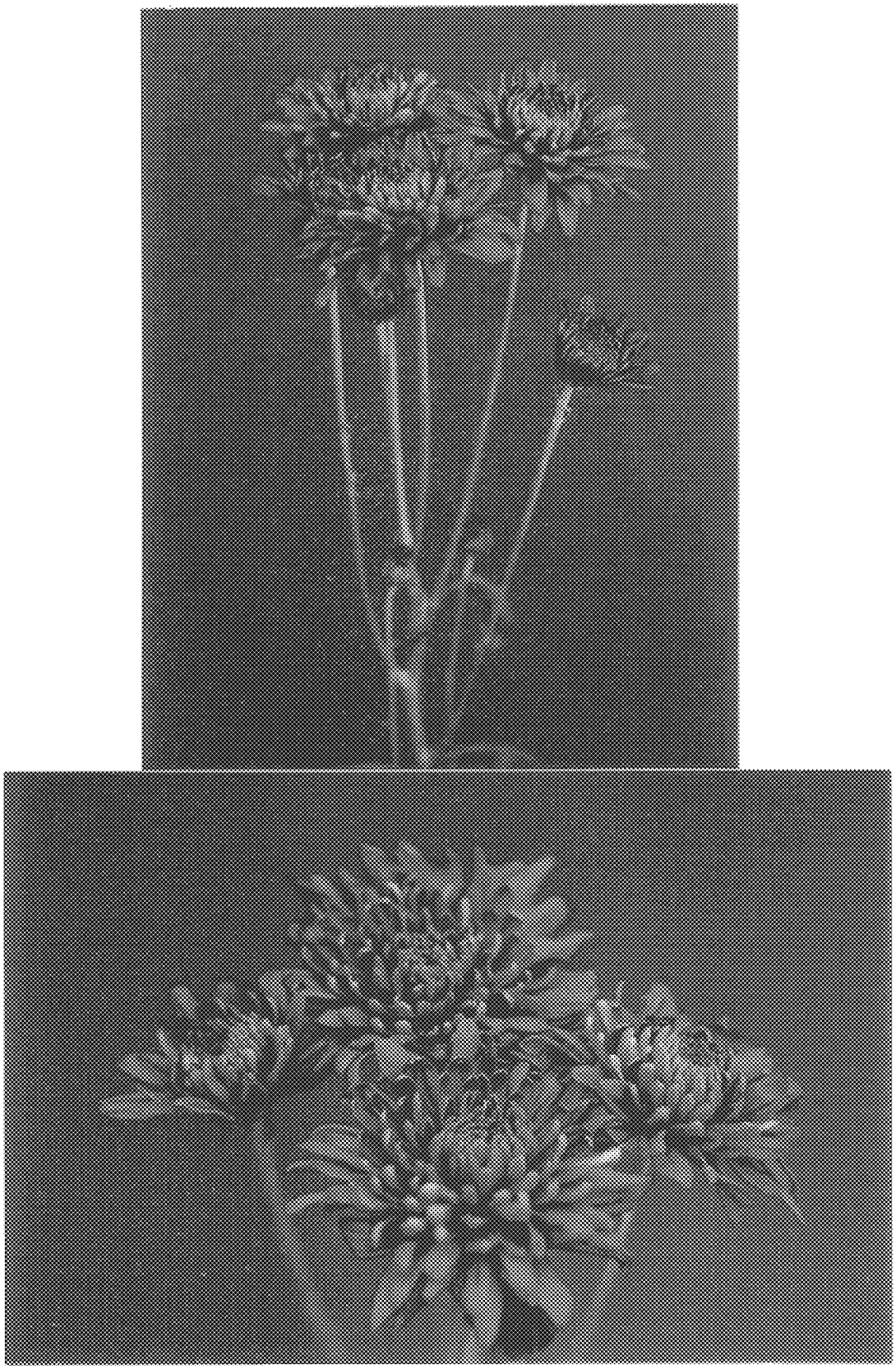

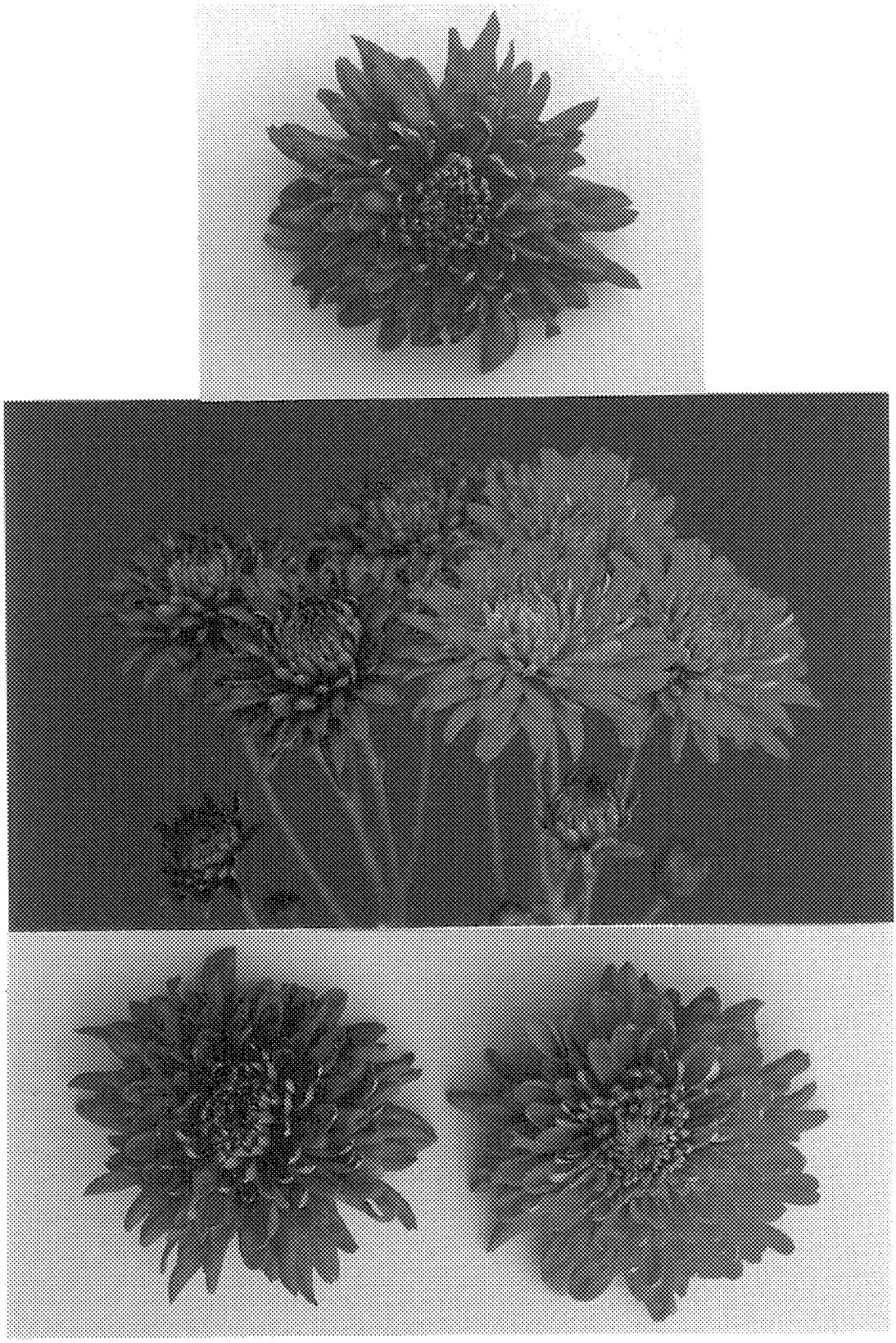

* * * * *